(12) United States Patent
Hervig

(10) Patent No.: US 10,251,472 B1
(45) Date of Patent: Apr. 9, 2019

(54) INFINITY BRUSH

(71) Applicant: Dana P. Hervig, Philipsburg, MT (US)

(72) Inventor: Dana P. Hervig, Philipsburg, MT (US)

( * ) Notice: Subject to any disclaimer, the term of this patent is extended or adjusted under 35 U.S.C. 154(b) by 276 days.

(21) Appl. No.: 15/161,378

(22) Filed: May 23, 2016

(51) Int. Cl.
| | |
|---|---|
| *A46B 13/00* | (2006.01) |
| *A46B 13/02* | (2006.01) |
| *B08B 1/00* | (2006.01) |
| *B08B 1/04* | (2006.01) |
| *A61C 17/24* | (2006.01) |
| *A61C 15/00* | (2006.01) |
| *A61C 15/04* | (2006.01) |
| *A47L 11/40* | (2006.01) |

(52) U.S. Cl.
CPC .............. *A46B 13/02* (2013.01); *A46B 13/00* (2013.01); *A47L 11/4047* (2013.01); *A61C 15/042* (2013.01); *A61C 15/047* (2013.01); *A61C 17/24* (2013.01); *B08B 1/002* (2013.01); *B08B 1/008* (2013.01); *B08B 1/04* (2013.01)

(58) Field of Classification Search
CPC ....... A46B 13/00; A46B 13/02; A46B 13/026; A46B 13/08; B08B 1/00; B08B 1/001; B08B 1/002; B08B 1/008; B08B 1/04; B08B 1/003; B08B 1/006; A61H 11/00; A61H 11/02; A61H 2011/005; A61H 15/00; A61H 15/0078; A61H 15/0085; A47L 23/02; A47L 11/4047; A47L 11/4069; A61C 17/22; A61C 17/24; A61C 17/26; A61C 17/40; A61C 15/042; A61C 15/047
USPC .... 15/21.1, 22.3, 30, 32, 34, 35, 36, 51, 80, 15/97.1, 97.2, 99; 601/112–113, 124, 601/132, 134, 135, 143, 144, 147; 132/322–329
See application file for complete search history.

(56) References Cited

U.S. PATENT DOCUMENTS

| | | | |
|---|---|---|---|
| 558,934 | A * | 4/1896 | Cowgill ............................ 15/51 |
| 582,509 | A | 5/1897 | Seufert |
| 827,965 | A | 8/1906 | Engel |
| 878,748 | A | 2/1908 | Scanlan |
| 997,113 | A | 7/1911 | Campbell |
| 1,180,172 | A | 4/1916 | Mitchell |
| 2,140,307 | A | 12/1938 | Belaschk et al. |
| 2,181,676 | A | 11/1939 | Wheeler |
| 2,247,440 | A | 7/1941 | Hempel |

(Continued)

FOREIGN PATENT DOCUMENTS

| | | | |
|---|---|---|---|
| DE | 10025109 | * | 12/2000 |
| DE | 19961447 | * | 7/2001 |

(Continued)

OTHER PUBLICATIONS

Partial machine translation of DE 19961447, Jul. 5, 2001.*

*Primary Examiner* — Mark Spisich
(74) *Attorney, Agent, or Firm* — Albert W. Watkins

(57) ABSTRACT

An infinity brush has a flaccid belt configured to define a lemniscate. A plurality of work-contacting segments protrude from and are carried by the flaccid belt. A mechanical drive rotates the flaccid belt. Various embodiments of the flaccid belt include a single lemniscate, a plurality of lemniscates, and various simulated lemniscates. In one embodiment, the infinity brush bristle includes non-cylindrical brush bristles with a longitudinal shaft having at least one diameter transition, while other bristles comprise beads of various oval, circular, and cylindrical geometries.

12 Claims, 7 Drawing Sheets

(56) References Cited

U.S. PATENT DOCUMENTS

| | | | | |
|---|---|---|---|---|
| 2,524,928 A | * | 10/1950 | Platz | A47L 11/14 15/320 |
| 3,158,885 A | * | 12/1964 | Kammann | A47L 11/292 15/51 |
| 3,252,175 A | | 5/1966 | Pedersen | |
| 3,387,311 A | * | 6/1968 | Blanc | A47L 23/02 15/36 |
| 3,686,699 A | | 8/1972 | Knestele | |
| 3,884,224 A | * | 5/1975 | Garcia | A61H 7/005 601/144 |
| 3,909,869 A | * | 10/1975 | Hukuba | A47L 11/33 15/41.1 |
| 4,084,280 A | | 4/1978 | May | |
| 4,156,620 A | | 5/1979 | Clemens | |
| 4,326,549 A | * | 4/1982 | Hinding | A61C 15/047 132/322 |
| 4,344,202 A | | 8/1982 | Hayat | |
| 5,016,660 A | * | 5/1991 | Boggs | A61C 15/047 132/322 |
| 5,063,948 A | * | 11/1991 | Lloyd | A61C 15/042 132/321 |
| 5,081,986 A | * | 1/1992 | In | A61H 7/006 601/144 |
| 5,217,031 A | * | 6/1993 | Santoro | A61C 15/046 132/322 |
| 5,316,028 A | * | 5/1994 | Flemming | A61C 15/043 132/321 |
| 5,943,725 A | * | 8/1999 | Wandres | B08B 1/008 15/102 |
| 6,032,313 A | | 3/2000 | Tsang | |
| 6,112,753 A | * | 9/2000 | Arsenault | A61C 15/042 132/321 |
| 6,266,841 B1 | * | 7/2001 | Cho | B43L 21/02 15/21.1 |
| 6,272,711 B1 | | 8/2001 | Ignacio | |
| 6,799,346 B2 | | 10/2004 | Jeng et al. | |
| 7,954,192 B2 | | 6/2011 | Gatzemeyer et al. | |
| 8,250,694 B2 | | 8/2012 | Gatzemeyer et al. | |
| 8,584,291 B2 | | 11/2013 | Thompson | |
| 8,636,677 B2 | | 1/2014 | Van Der Rijt et al. | |
| 8,677,542 B1 | | 3/2014 | Whillock | |
| 8,683,639 B2 | | 4/2014 | Khudoley | |
| 2004/0231077 A1 | * | 11/2004 | Richmond | A46B 5/06 15/22.3 |
| 2008/0029122 A1 | * | 2/2008 | Egeresi | A61C 15/047 132/322 |
| 2010/0325821 A1 | * | 12/2010 | Mann | A47L 1/02 15/21.1 |
| 2011/0259360 A1 | * | 10/2011 | Marvin | A61C 15/043 132/325 |
| 2015/0272711 A1 | * | 10/2015 | Gagan | A61C 15/042 132/329 |

FOREIGN PATENT DOCUMENTS

| | | | |
|---|---|---|---|
| FR | 1415597 | * | 10/1965 |
| FR | 2215190 | * | 8/1974 |
| JP | 9-248215 | * | 9/1997 |

* cited by examiner

INFINITY BRUSH

BACKGROUND OF THE INVENTION

1. Field of the Invention

The present invention pertains generally to brushing, scrubbing, and general cleaning, and more particularly to an improved bristles and brushes that enhance the brushing and cleaning experience.

2. Description of the Related Art

Brushing is an age-old technique that is used for many purposes, including but not limited to cleaning, shaping, texturing, polishing, and even ice melting such as performed in the sport of curling. The vast majority of brushing applications rely upon contact between a surface being treated and the ends of a plurality of longitudinally extensive bristles. The bristle ends will form an abrupt edge, and the bodies of the bristles will be slightly spring-loaded, thereby ensuring that the bristle ends stay in contact with a surface, even if the surface is slightly irregular.

These bristles are often provided in a plurality of individually bound groups or clusters. Many modern brushes are formed by transversely cutting a plurality of parallel strands into relatively shorter segments, and then folding or crimping this cluster of strands in half. The folded or crimped cluster is then pressed into a brush body hole, or molded into the body in one way or another. The clusters of bristles are often located in relation to adjacent groups or clusters of brush bristles by the brush body, a holder, or the like. As a result, while the outer bristles are exposed fully along their length, the majority of bristles are instead primarily only exposed adjacent to their ends. When the brush bristles are then pressed against and moved relative to a surface, the abrupt edge of the bristle ends is then pressed into contact with the surface, generating quite high forces in the relatively small surface area points of contact. This is very useful to dislodge debris from a surface when cleaning the surface, or to create enough very local heat to provide limited ice melting such as in the sport of curling. In addition, the many individual bristles will move through a viscous fluid with very limited fluid displacement adjacent the bristle ends, while the displaced fluid elevates with respect to the surrounding fluid. As a result, this process creates a surface texture that is simply known as a "brushed finish".

Unfortunately, with either or both of age and excessive brushing force, the outer bristles will tend to deform away from the clusters, tending to flatten. This can also happen temporarily and reversibly during use, when the force applied to the brush is sufficiently great to exceed the stiffness of the plurality of bristles. In other words, at some sufficient force, the individual strands that form the brush bristles will flex, and the brush will flatten. Once this occurs, these deformed bristles become much less useful and productive. This is because the point of contact changes when the brush flattens from the abrupt transition formed by the transverse cut at the ends of the bristles to the long smooth side of the bristle.

In addition to permanent flattening or deformation of the brush bristles, another sometimes challenging or alternatively sometimes beneficial feature of the brush is the fact that the brush will typically be pressed and drawn in such a way that the cut end of each bristle will follow in a line parallel to that defined by other bristles. This is a primary benefit in surface texturing, such as the "brush finish" described herein above, since the lines of texture will follow the direction the brush is moved. A person may then easily control the pattern of the brushed finish, simply by controlling the direction of movement of the brush. This is also of benefit in moving debris in a common direction to a collection location, where the debris may then be scooped up or otherwise handled.

However, when cleaning a surface it is of great benefit to be able to contact the surface from different directions. When debris is adhered to a surface, contacting the debris from at least two different directions is of special benefit, leading to much greater debris removal. A small ridge will cause the bristle to lift and snap over the top of the of the ridge, leaving a shadow of debris parallel to and in the lee of the small ridge. When a bristle then comes from a perpendicular direction, and particularly when the bristle hits the shadow of debris before the ridge, then the shadow of debris will more likely be removed. Similar effect can occur with depressions in a surface, and with movement of bristles over tightly adhered debris, and in each case, a substantially perpendicular direction travel of bristles or even an opposed direction is highly beneficial.

Recognizing the benefit of moving bristles in different directions over a surface, a number of artisans have designed brushes that include brush blocks that rotate or move. The following US patents, the teachings and contents of each which are incorporated herein by reference, are exemplary: U.S. Pat. No. 2,140,307 by Belaschk et al, entitled "Electrically operated combination set for the dressing table"; U.S. Pat. No. 4,084,280 by May, entitled "Tooth brush"; U.S. Pat. No. 4,156,620 by Clemens, entitled "Apparatus and method for cleaning teeth"; U.S. Pat. No. 4,344,202 by Hayat, entitled "Electric toothbrush"; U.S. Pat. No. 6,799,346 by Jeng et al, entitled "Toothbrush with oppositely reciprocating brush heads"; U.S. Pat. No. 7,954,192 by Gatzemeyer et al, entitled "Powered toothbrush with rotating sections"; U.S. Pat. No. 8,250,694 by Gatzemeyer et al, entitled "Powered toothbrush with rotating sections"; U.S. Pat. No. 8,584,291 by Thompson, entitled "Whole mouth toothbrush"; U.S. Pat. No. 8,677,542 by Whillock, entitled "Interchangeable tooth brush system and associated method for promoting oral health"; and U.S. Pat. No. 8,683,639 by Khudoley, entitled "Mechanical toothbrush and drive mechanism therefor (embodiments)". While these work admirably for many applications, they are not without limitations. As but one example, where the brush blocks rotate, this ensures complex movement of the bristles over a surface. This is highly desirable for many applications. However, along edges the bristles will in fact only move substantially in a single direction, running parallel to the edge.

Again, for many applications, this is of little or no consequence. However, in more critical applications, such as in the case of tooth brushing for patients with afflictions such as gingivitis, it may be critical to remove as much of the debris as possible from the tooth surface and within the gingival pockets. For such an application, having bristles moving in more than one direction is of great benefit. For those situations, the counter-rotating bristle blocks are highly beneficial, such as illustrated by Belaschk et al; Clemens; Jeng et al; and several others incorporated herein above. While these brushes offer substantial improvement over many of the prior brushing apparatus, once again along an edge there is only minimal contact. In other words, as the brush traverses across the tooth, with the brush in contact with the gingival tissue, only a few of the bristles located about the outer diameter are in contact with the tooth along this edge. For exemplary purposes, only ten or fifteen degrees of the 360 degrees of outer diameter bristles in a circular bristle block may be in contact with an edge. The exact angle of bristles in contact will depend upon a number of variables, but it should be apparent that just a small part of the diameter of the brush head is active adjacent the edge. In contrast, at a distance form the edge defined by half the diameter of the brush block, the entire diameter of bristles are active. In other words, the brushing at one-half the diameter of the bristle block is many times more intense and thorough than along the gingival tissue. Unfortunately, for patients with gingivitis, this creates a dilemma. Either they must spend many times the amount of time brushing, or tolerate the less thorough cleaning of debris along the gingival tissue. Neither option is particularly desirable.

Other US patents, the teachings and contents of each which are incorporated herein by reference, illustrate endless belt brushes, including: U.S. Pat. No. 997,113 by Campbell, entitled "Shoe polishing machine"; U.S. Pat. No. 2,247,440 by Hempel, entitled "Scalp massaging device"; U.S. Pat. No. 3,252,175 by Pedersen, entitled "Electrically operated hair brush"; and U.S. Pat. No. 6,272,711 by Ignacio, entitled "Multifunction surface engaging apparatus that is particularly suited in removing snow and ice". Additional US patents, the teachings and contents of each which are incorporated herein by reference, illustrate endless belt brushes with specially noted brush belt drives: U.S. Pat. No. 582,509 by Seufert, entitled "Can washing machine"; U.S. Pat. No. 878,748 by Scanlan, entitled "Brush"; U.S. Pat. No. 1,180,172 by Mitchell, entitled "Brushing machine"; U.S. Pat. No. 2,181,676 by Wheeler, entitled "Shoe polishing machine"; U.S. Pat. No. 3,686,699 by Knestele, entitled "Device for cleaning carpeted floors". Endless belts are particularly beneficial where an even distribution of bristle contact across an area is desired. Consequently, many of these patents are equally effective adjacent an edge as they are in the center of the brush. However, these apparatus also generally lose the benefit of contacting a surface from many directions, and instead the contact is primarily linear along a single axis.

One US patent, the teachings and contents of each which are incorporated herein by reference, illustrates both rotary, linear reciprocating, and endless belt brushes: U.S. Pat. No. 6,032,313 by Tsang, entitled "Household appliance having plural coaxially rotatable or parallel linearly movable heads or tools".

Two additional patents of general interest, the teachings and contents of each which are incorporated herein by reference, include: U.S. Pat. No. 827,965 by Engel, entitled "Tooth brush"; and U.S. Pat. No. 8,636,677 by Van Der Rijt et al, entitled "Intraoral appliance for cleaning teeth".

In addition to the aforementioned patents, Webster's New Universal Unabridged Dictionary, Second Edition copyright 1983, is incorporated herein by reference in entirety for the definitions of words and terms used herein.

SUMMARY OF THE INVENTION

In a first manifestation, the invention is a brush bristle. The brush bristle has a longitudinal shaft having a first end and a second end longitudinally distal to the first end. An edge exists at the juncture between the longitudinal shaft and first end. At least one diameter transition is provided between the said first and second ends.

In a second manifestation, the invention is a bristle belt. The belt has a flaccid endless loop. A plurality of brush segments are securely carried by the loop.

In a third manifestation, the invention is a brush. The brush has a flaccid belt configured to define a lemniscate. A plurality of work-contacting segments protrude from and are carried by the flaccid belt. A mechanical drive rotates the flaccid belt.

OBJECTS OF THE INVENTION

Exemplary embodiments of the present invention solve inadequacies of the prior art by providing improved non-cylindrical brush bristles, bristle belts formed from a loop and provided with a half-twist to form a shape resembling an infinity sign, and brushes incorporating a drive apparatus and various combinations of non-cylindrical brush bristles and bristle belts.

The present invention and the preferred and alternative embodiments have been developed with a number of objectives in mind. While not all of these objectives are found in every embodiment, these objectives nevertheless provide a sense of the general intent and the many possible benefits that are available from embodiments of the present invention.

A first object of the invention is to provide improved bristles and brushes that enhance the brushing and cleaning experience. A second object of the invention is to provide an improved brush bristle that does not significantly lose efficacy with age or application of extraordinary forces thereto. Another object of the present invention is to provide an improved brush bristle belt that moves brush bristles in a lemniscate pattern. A further object of the invention is to provide a brush that may incorporate these improved brush bristles and brush bristle belts while also being readily configured for a variety of functions, including but not limited to cleaning, shaping, texturing, polishing, and even ice melting such as performed in the sport of curling. Yet another object of the present invention is to provide both full lemniscate geometries and optional simulated lemniscates. In some embodiments, another object of the invention is to provide equal and opposed forces from a plurality of brush bristles.

BRIEF DESCRIPTION OF THE DRAWINGS

The foregoing and other objects, advantages, and novel features of the present invention can be understood and appreciated by reference to the following detailed description of the invention, taken in conjunction with the accompanying drawings, in which.

DESCRIPTION OF THE PREFERRED EMBODIMENT

Manifested in the preferred and alternative embodiments, the present invention provides an infinity brush that provides novel bristle construction and movement with respect to an object or work surface being brushed, swabbed, massaged, or otherwise contacted.

Figure 1:
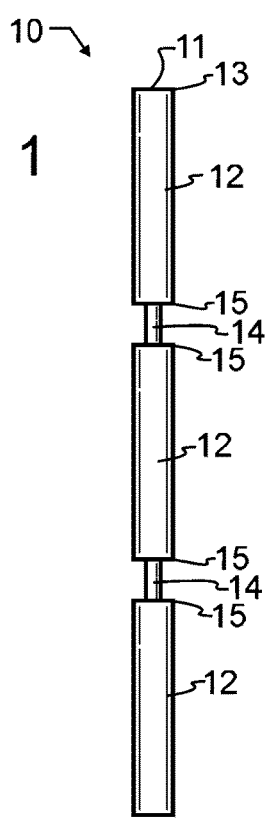
FIG. 1 illustrates a preferred embodiment bristle designed in accord with the teachings of the present invention from a side elevational view.

FIG. 1 illustrates a preferred embodiment bristle 10 that provides a typical transversely cut end 11 defining an edge 13 that is defined by longitudinal shaft 12. However, and as noted herein above, with prior art bristles, overt time the bristle will soften and flex, and edge 13 may contact the surface from an angle or orientation that follows the outer periphery of shaft 12, rather than presenting a sharp edge and point of contact along edge 13. Said another way, as a bristle ages and tends to flatten, contact changes from adjacent transverse cut edge 11 to the outer diameter of shaft 12, along the outer cylindrical geometry. As may immediately be recognized or understood, this will spread the contact area over a much larger surface area, and the lack of sudden discontinuity means that debris will not likely be displaced by this gentle rubbing of shaft 12. However, in the case of bristle 10, one or more narrowed segments 14 that define a diameter transition are provided, that each define sharp edges 15 in shaft 12. Consequently, when bristle 10 flattens, either due to age or to large force being applied to bristle 10, then sharp edges 15 will become active and will assist in the brushing action. While two of these narrowed segments 14 are illustrated, there may be any number from one to many of these narrowed segments 14. They may be very close to transverse cut edge 11, or spaced therefrom. They may also be equidistantly spaced, or may be clustered adjacent to transverse cut edge 11.

Figure 2:
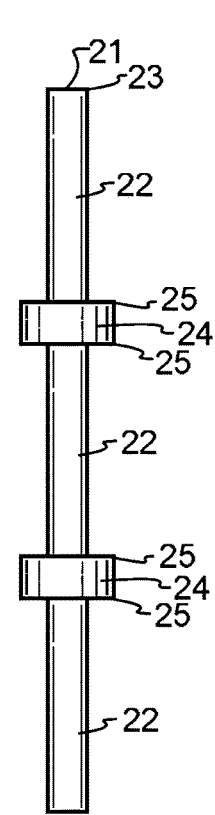
FIG. 2 illustrates a first alternative embodiment bristle designed in accord with the teachings of the present invention from a side elevational view.

FIG. 2 illustrates a first alternative embodiment bristle 20 designed in accord with the teachings of the present invention. Bristle 20 has a transverse cut 21 defining one end of the bristle, and an edge 23 at the juncture between transverse cut 21 and shaft 22 which defines the usually active sharp transition that contacts surfaces and displaces or removes debris. Instead of narrowed segments 14, bristle 20 incorporates ribs 24 that are of larger diameter than shaft 22. This also defines additional sharp edges 25 that, like sharp edges 15, will become active any time bristle 20 is pressed against an object or work surface onto the outer diameter of shaft 22, rather than along edge 23. Like narrowed segments 14, at least one but many ribs 24 may be provided at any suitable locations and spacings.

While a sharp edge 15, 25 is illustrated and preferred, it will be understood herein that more gentle transitions may in an alternative embodiment also be provided. In one alternative, bristle 20 may be configured to resemble a ringed nail. Furthermore, in various additional alternative embodiments, other means to provide a textured surface to shafts 12, 22 are also contemplated, including roughening the exterior of the shaft or other suitable technique. In addition, while cylindrical shafts 12, 22 are illustrated, any cross-sectional geometry may also be used, including for exemplary and non-limiting purpose, strips having more rectangular cross-section or the like.

Figure 3:
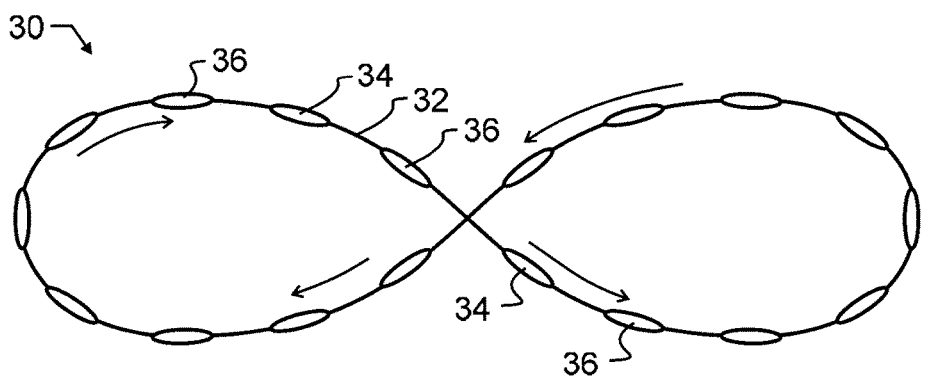
FIG. 3 illustrates a preferred embodiment bristle belt arranged in an infinity loop designed in accord with the teachings of the present invention from a top plan view.
Figure 8:
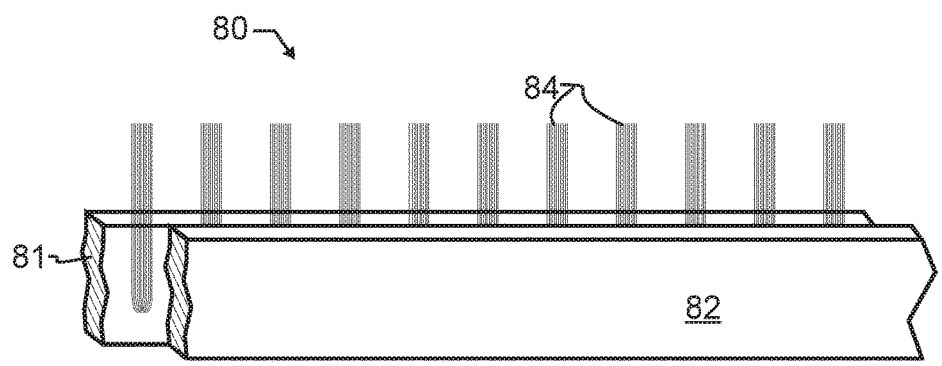
FIG. 8 illustrates a segment of a fourth alternative embodiment bristle belt designed in accord with the teachings of the present invention from a projected and partially sectioned view.

FIG. 3 illustrates a preferred embodiment bristle belt 30 arranged in an infinity loop, also referred to as a "FIG. 8" or a lemniscate. As described herein above, one challenge with brushes is providing a brushing motion from different directions, particularly in restricted spaces. Bristle belt 30 overcomes this challenge by providing a flaccid and reasonably durable belt 32 having a plurality of brush segments 34, 36 secured to move with belt 32. Exemplary motion is shown by the arrows in FIG. 3, and as may be apparent then, the left portion of the loop moves in a generally clockwise manner, while the right portion of the loop moves in a generally counter-clockwise manner. In a crowded location, such as in the lower or upper jaw adjacent to the gums, electric toothbrushes of the prior art will only move in one direction with respect thereto, or only very slightly oscillate as in the case of the Van Der Rijt et al patent. In the few instances where round bristle blocks are provided that counter-rotate, the point of contact adjacent the gum line will be exactly that, a point at the top of the circular brush block. In contrast, bristle belt 30 will provide not only the benefit of movement in different and complex directions, including both rotary and more nearly linear movement, it will also provide an extended track adjacent an edge or boundary, such as along the gum line within a mouth, which will move in multiple directions along that edge or boundary.

Another challenge with rotary brush blocks, particularly those having just one block or several that all rotate in the same direction, is that if less than the entire brush is in contact with a surface, or if the cut ends of the bristles are not loaded to be parallel to the plane of the work surface, the bristles will then tend to push or move the brush around. In the case of the lemniscate configuration of FIG. 3, if an edge is adjacent either the top or bottom of the lemniscate as viewed in FIG. 3, then even if bristle belt 30 is titled towards the top or bottom the left and right loops will counteract each other, and bristle belt 30 will not tend to walk or drive across a surface.

Belt 32 may for exemplary purposes comprise a mono- or multi-filament strand formed into a continuous loop. Exemplary materials might include various polymers such as nylon, polyester, and other polymers, but might also include other materials such as steel and other metals, or natural fibers such as cotton, jute, hemp, or the like. To form a lemniscate, or infinity symbol geometry from a simple circle, the belt 32 may be wrapped about a pulley and extended therefrom. Then the free half of the endless loop is given a one-half turn, making the top of the belt the bottom in that rotated half. This preserves the endless belt movement, but causes the familiar overlap of a lemniscate midway on the belt.

Figure 4:
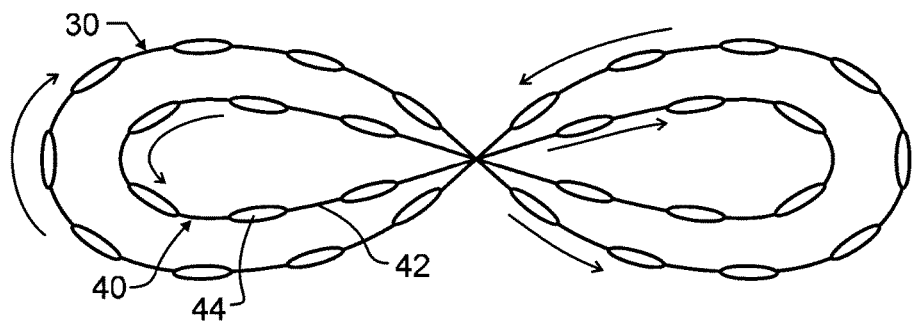
FIG. 4 illustrates a first alternative embodiment bristle belt arranged in a double parallel and counter-rotating infinity loop designed in accord with the teachings of the present invention from a top plan view.
Figure 5:
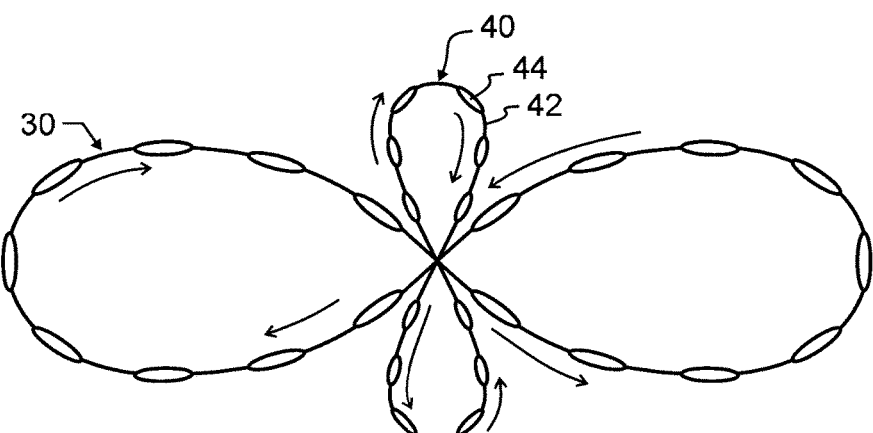
FIG. 5 illustrates a second alternative embodiment bristle belt arranged in a double perpendicular infinity loop designed in accord with the teachings of the present invention from a top plan view.

Bristle belt 30 may be provided with any of a wide variety of brush segments 34, 36. For exemplary purposes only, and not solely limiting the invention thereto, these segments may comprise small oval beads as illustrated, round beads, cylindrical beads, brush blocks, or even discs similar to those found on candy necklaces. In fact, any known geometry that a designer may find acceptable for a particular application will be understood to be incorporated herein. Likewise, many different materials may also be used. Silicone is one preferred material, particularly where oval beads such as illustrated in FIGS. 3-5 are used. Nevertheless, the invention is not so limited, and a wide variety of materials ranging from brushes to brush balls, soft cloth balls, or pads are contemplated herein, again depending entirely upon the object to be treated. Again for exemplary and non-limiting purposes, it is contemplated herein that brush segments 34, 36 might be comprised by a soft and absorbent material such as wool or cotton that may then be used to buff or polish diverse surfaces including but not limited to plastics, glass, and various metals.

In an even further embodiment, brush segments 34, 36 may be of different sizes or geometries. For exemplary purposes, brush segment 34 might be of a first diameter, while brush segment 36 might be of a second larger diameter. In such case, then bristle belt 30 as it move over a surface will alternate between larger brush segments 36 and smaller brush segments 34. This varying geometry may be used advantageously to create a pulsating effect of slightly greater contact forces with brush segments 36 and slightly lesser contact forces with brush segments 34. With different compositions, the characteristics may vary. Once again, for exemplary and non-limiting purpose, brush segments 34 might be more absorbent and so may transport more liquid, including cleaning liquids or pastes, while brush segments 36 might be moisture impervious, and so remove any moisture including cleaning fluids. This alternating contact with a surface can be designed and configured for particular purposes to have many benefits.

FIG. 4 illustrates preferred embodiment bristle belt 30 in further combination with a second bristle belt 40. In this arrangement, the two bristle belts 30, 40 counter-rotate with respect to each other, thereby even further improving the coverage provided by these belts. In addition, the counter-rotation of belt 40 tends to cancel the forces that might otherwise lead to a brush pulling or "walking" across a surface or object. As described above with reference to FIG. 3, tilting toward the top or bottom of bristle belt 30 will lead to fully canceled forces. However, tilting to either the right or left as illustrated in FIG. 3 will lead to an unbalanced force that will either drive bristle belt 30 down if tilted to the left, or up if tilted to the right. In contrast, the counter-rotation of bristle belt 40 will tend to cancel this motion. More complete cancellation may be achieved by either driving belt 40 faster than belt 30, such as by using a larger drive sprocket or cogged wheel, or alternatively by providing either more or wider clusters of bristles, to increase the surface contact area of the bristles of bristle belt 40 with respect to bristle belt 30.

FIG. 5 illustrates an alternative embodiment arrangement where the two bristle belts 30, 40 are arranged in infinity loops perpendicular to each other. Brush segments 44, securely driven by flaccid and reasonably durable belt 42, may be of like composition and geometry to brush segments 34, 36, or may alternatively be of either or both of different composition and geometry.

While FIGS. 4 and 5 are described and illustrated as comprising two distinct bristle belts 30, 40, it will be understood that the provision of extra appropriately positioned half-turns will permit the fabrication of these dual lemniscate arrangements from a single bristle belt as well.

Figure 6:
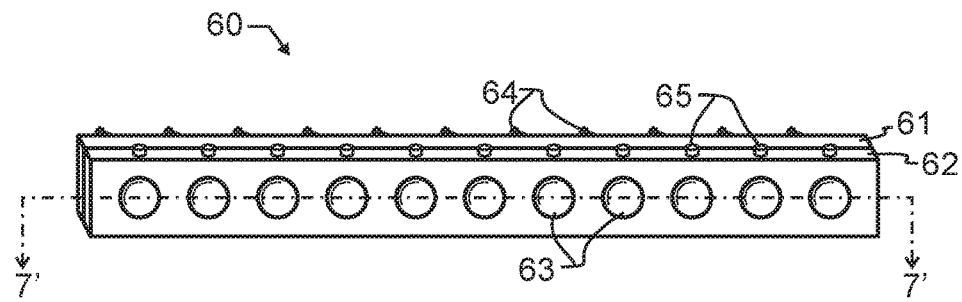
FIG. 6 illustrates a segment of a third alternative embodiment bristle belt designed in accord with the teachings of the present invention from a top plan view.
Figure 7:
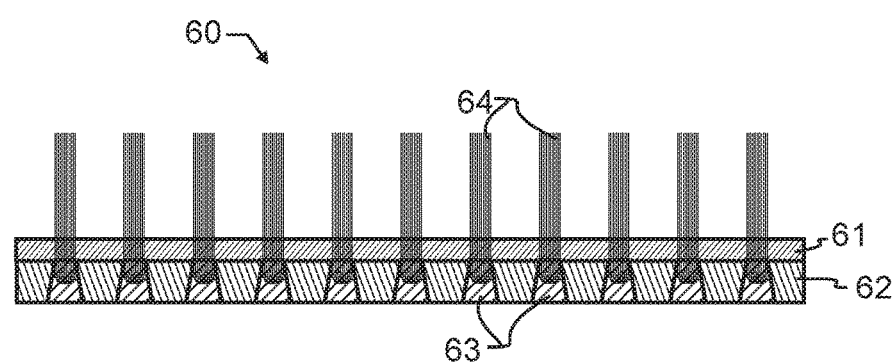
FIG. 7 illustrates the third alternative embodiment bristle belt segment of FIG. 6 by sectional view taken along section line 7' of FIG. 6.

FIGS. 6 and 7 illustrate a segment of a third alternative embodiment bristle belt 60. A softer brush belt 61 may be provided, and have a plurality of bristles 64 inserted into and passing through. A potentially harder drive belt 62 may be securely laminated thereto. In one embodiment, drive belt 62 may first be fabricated, having conical openings therein. Next, bristles 64 may be placed therein, and brush belt 61 may be molded, simultaneously forming both belt 61 and conical plugs 63. In an alternative embodiment, bristles 64 may be preformed with and molded into slightly conical plugs 63, which are in turn inserted or molded into drive belt 62. In either case, this slightly conical geometry helps to ensure that bristles 64 do not pull out of harder drive belt 62. To facilitate driving belt 60 from a side face, perpendicular to bristles 64, additional features may be provided such as small dimples 65 or any other features known in the art of drive belts to assist in the engagement and driving by a sheave other belt drive mechanism.

To form a lemniscate, or infinity symbol geometry from a simple circle, bristle belt 60 must be formed already in the geometry, or preferably by forming the belt with half the bristles pointing up, and the other half down. Then, when bristle belt 60 is wrapped about a pulley and extended therefrom, and then the free half of the endless loop given a one-half turn, making the top of the belt the bottom in that rotated half, the half with the bristles pointing down will thereby be returned to an upward position. This preserves the endless belt movement, and aligns all bristles up, but also causes the familiar overlap of a lemniscate midway on the belt.

FIG. 8 illustrates a segment of a fourth alternative embodiment bristle belt 80. In this embodiment, bristles 84 are secured between to belts 81, 82. Belts 81, 82 may each have geometry similar to a standard drive belt or rubber band, but the two are laminated together. At the time of lamination, bristle clusters 84 are inserted there between, and in the process of bonding, vulcanizing, or other suitable technique, bristle clusters 84 are permanently secured therein. As with belt 60, one half of the bristles must be oriented downward, and the other half upward, if the belt is formed in a circle, to permit the half twist required to form the lemniscate.

Figure 9:
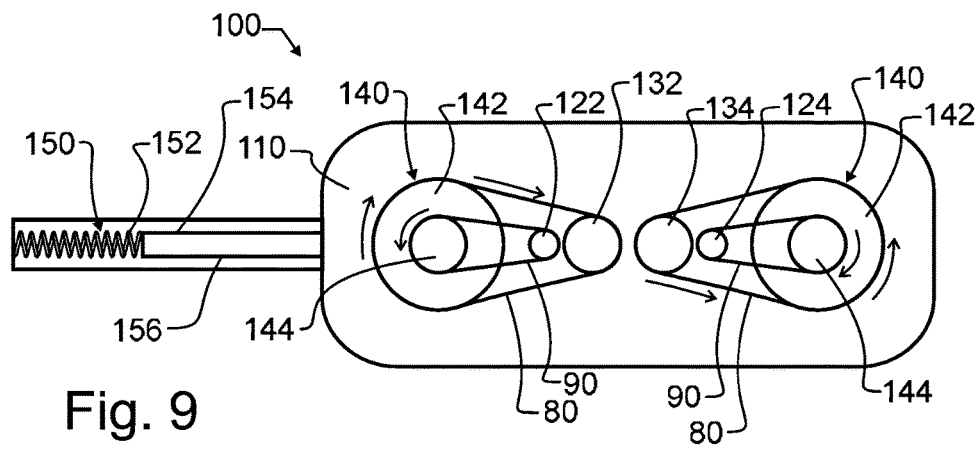
FIG. 9 illustrates a preferred embodiment brush designed in accord with the teachings of the present invention from a top plan view.

FIG. 9 illustrates a preferred embodiment brush 100 designed in accord with the teachings of the present invention from a top plan view. As illustrated therein, a brush body 110 supports a pair of drive pulleys 140. Each drive pulley may optionally be configured to include to drive belts, by incorporating a smaller diameter top 144 and a larger diameter lower portion 142, in the manner of a layer cake. In this case, each drive pulley 140 will engage with two belts 80, 90. Each of the belts is then coupled to an associated idler roller 124, 134. As may be apparent, belts 80, 90 are configured in the general geometry of a tear drop shape. This does not define a full lemniscate geometry. However, and as may have been apparent form the illustrations of FIGS. 3-5, a full lemniscate requires an intersection between the two half loops. With the oval beads of FIGS. 3-5, this is possible without severe detriment. There will be slight "bumps" in the drive force required as brush segments 34, 36, 44 pass over the vertex or point of intersection between the two loops, but with appropriate design and materials, this would still function properly. However, when more severe edges are provided, such as with cylindrical beads, or with brushes extending transversely in an abrupt manner from the belts, this distinct overlap of a true and complete lemniscate is not practically possible. Consequently, and as illustrated in FIG. 9, the pair of tear drop shaped belt arrangements provides a very close simulation to a full lemniscate, while avoiding the actual overlap at the vertex.

In addition, and as discussed herein above with respect to FIG. 4, the dual lemniscate as illustrated in FIG. 9 with counter-rotating bristle belts 80, 90, helps to provide equal and opposed forces from a plurality of brush bristles, to prevent the generation of unbalanced forces that might otherwise cause the entire brush to be driven across a work surface.

A belt tensioning apparatus 150 is provided, which, as will be described herein below with regard to FIG. 11, may be used to ensure tension in belts 80, 90. In addition, and while not illustrated, a mechanical drive such as is known from the prior art incorporated by reference herein above will be provided to turn drive pulleys 140. Noteworthy here, and throughout the various preferred and alternative embodiments illustrated, is that the preferred bristle belts and bristles are omni-directional. This means that the drive direction may be reversed. Consequently, while arrows are provided in the illustration for a particular drive direction, it is further contemplated herein that the drive arrows could all be reversed, if the drive motor were reversed.

Figure 10:
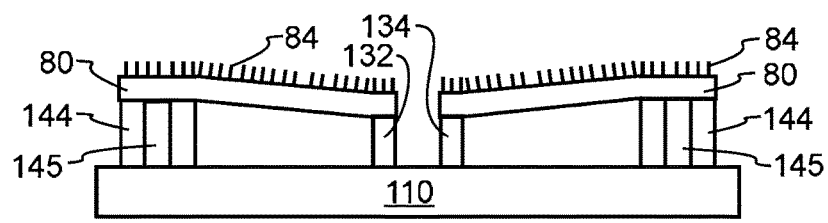
FIG. 10 illustrates the preferred embodiment brush of FIG. 9 from a side elevational view.

FIG. 10 illustrates the preferred embodiment brush of FIG. 9, but in a simplified form only illustrating a single bristle belt 80. Visible therein are drive features 145 formed within drive pulleys 144. These drive features 145 are illustrated as simple grooves cut into pulleys 144, though they may also take the form of full notches, defining the tops of pulleys 144 as castellations, similar to the top of a rook piece from a chess game, or as notches, cogs, or sprockets. The particular geometry of features 145 is not critical, and several alternatives are illustrated in the present figures. Nevertheless, these features may interact with either brush segments such as 34, 36, 44, or with small dimples 65 of bristle belt 60 to provide more powerful drive with less chance of belt slippage.

In FIG. 10, belts 80 adjacent to idler rollers 132, 134 may be lowered slightly relative to drive pulleys 144. This optional feature de-emphasizes the bristle force in the center of the lemniscate, thereby diminishing the less than perfect portion of the lemniscate simulation.

Figure 11:
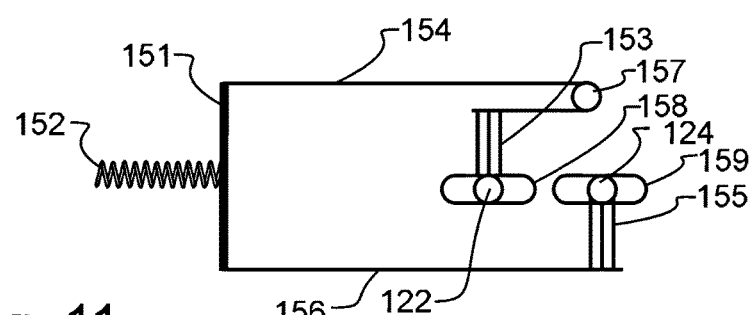
FIG. 11 illustrates a preferred brush belt tensioning apparatus used in the preferred embodiment brush of FIG. 9 from a simplified top plan view.

FIG. 11 illustrates the preferred brush belt tensioning apparatus used in the preferred embodiment brush 100 of FIG. 9. As shown therein, an extension spring 152 is shown extending between an anchor in the handle of brush 100 and plate 151. Plate 151 in turn couples securely to cables 154, 156. Cable 156 directly connects to linkage 155, which links to idler roller 124. While only shown linking to idler roller 124, it will be understood that idler roller 134 may also be engaged by linkage 155, or may alternatively be provided with a separate cable and linkage. Spring 152 is pulling these idler rollers 124, 134 towards spring 152, and thereby tensioning the associated belts 80, 90. Likewise, cable 154 is coupled to linkage 153, and from there to idler roller 122 (and optionally 132). However, idler rollers 122, 132 need pulled in the opposite direction, s a reversing pulley 157 is provided that reverses the direction of force to pull idler rollers 122, 132 away from spring 152. Guide slots 158, 159 are one of many exemplary ways to provide proper tracks to ensure that the idler rollers move linearly to tension the belts while still maintaining the respective generally tear drop or half-lemniscate geometries.

Various embodiments of brushes designed in accord with the present invention have been illustrated in the various FIGS. 10-16. The embodiments are distinguished by the hundreds digit, and various components within each embodiment designated by the ones and tens digits. However, many of the components are alike or similar between embodiments, so numbering of the ones and tens digits have been maintained wherever possible, such that identical, like or similar functions may more readily be identified between the embodiments. If not otherwise expressed, those skilled in the art will readily recognize the similarities and understand that in many cases like numbered ones and tens digit components may be substituted from one embodiment to another in accord with the present teachings, except where such substitution would otherwise destroy operation of the embodiment. Consequently, those skilled in the art will readily determine the function and operation of many of the components illustrated herein without unnecessary additional description.

Figure 12:
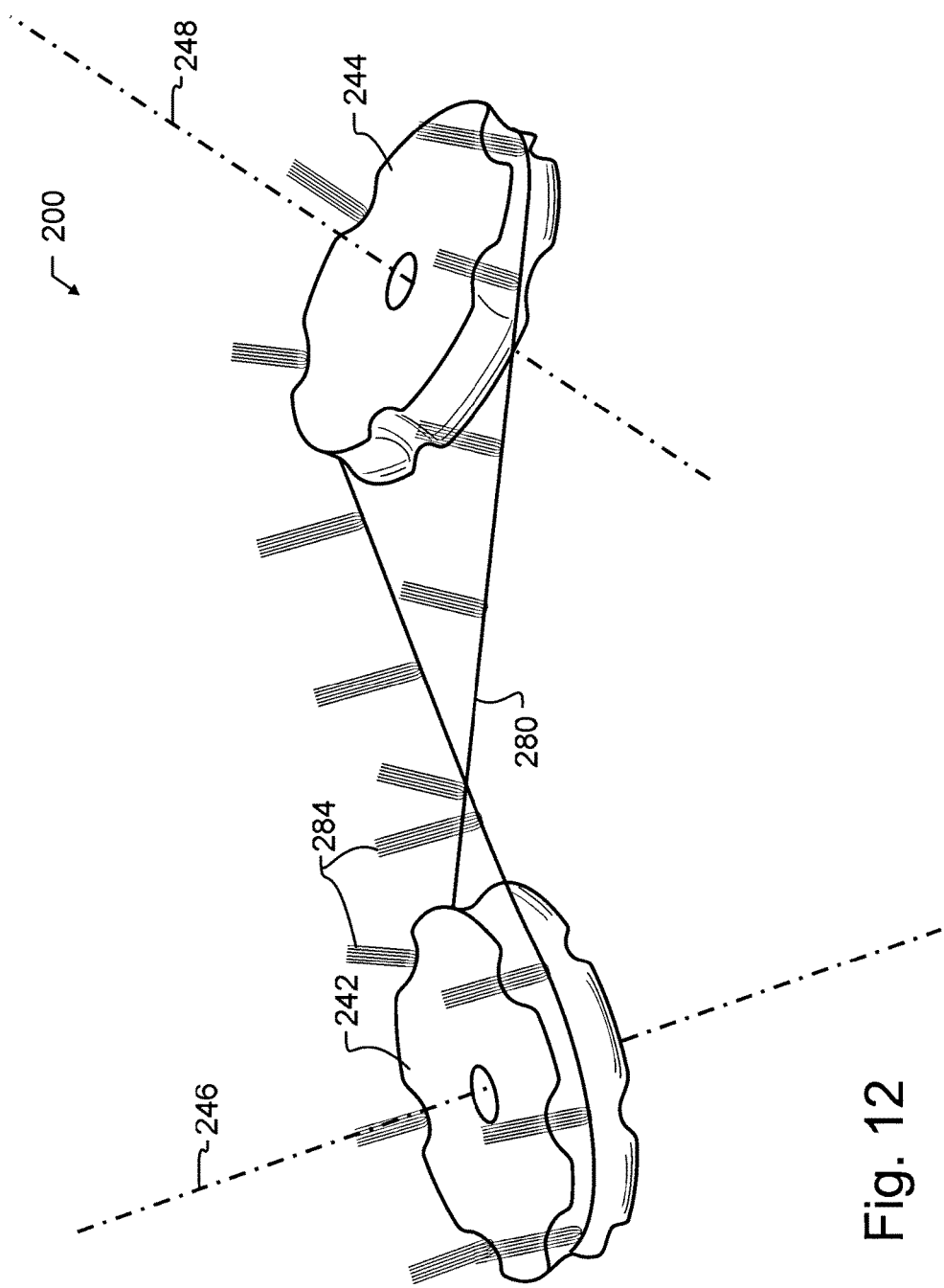
FIG. 12 illustrates a first alternative embodiment brush designed in accord with the teachings of the present invention from a simplified projected view.

FIG. 12 illustrates a first alternative embodiment brush designed in accord with the teachings of the present invention from a simplified projected view. In this case, a modified lemniscate is illustrated, wherein pulley 242 has an axis of rotation 246 that is offset from the axis of rotation 248 of pulley 244. This angular offset permits bristle belt 280 to move in a generally lemniscate pattern when viewed from a top plan view, but which in fact displaces the two directions of belt travel so that bristles 284 will not interfere with belt 280 while belt 280 rotates. As visible therein, a plurality of cogs may optionally be provided about each of pulleys 242, 244.

Figure 13:
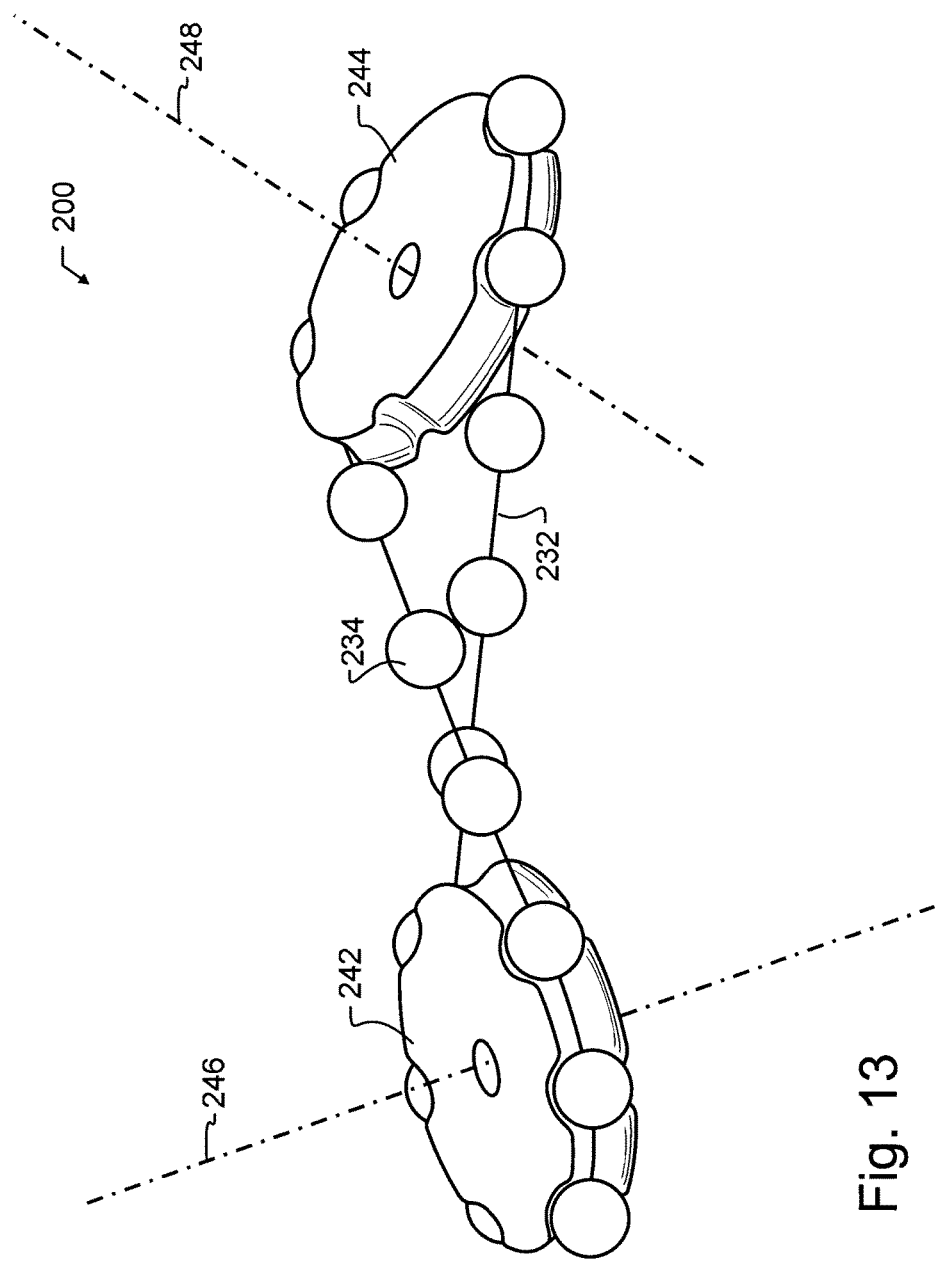
FIG. 13 illustrates a second alternative embodiment brush designed in accord with the teachings of the present invention from a simplified projected view.

FIG. 13 illustrates a second alternative embodiment brush 200 very similar to brush 200 of FIG. 12, including like pulleys 242, 244, but with bristle belt 280 replaced with a bristle belt 232 having large balls 234 affixed thereon. In this case, the angle of rotational axes 246, 248 may be more similar or more nearly parallel, since the balls 234 do not extend as far transversely from belt 232.

Figure 14:
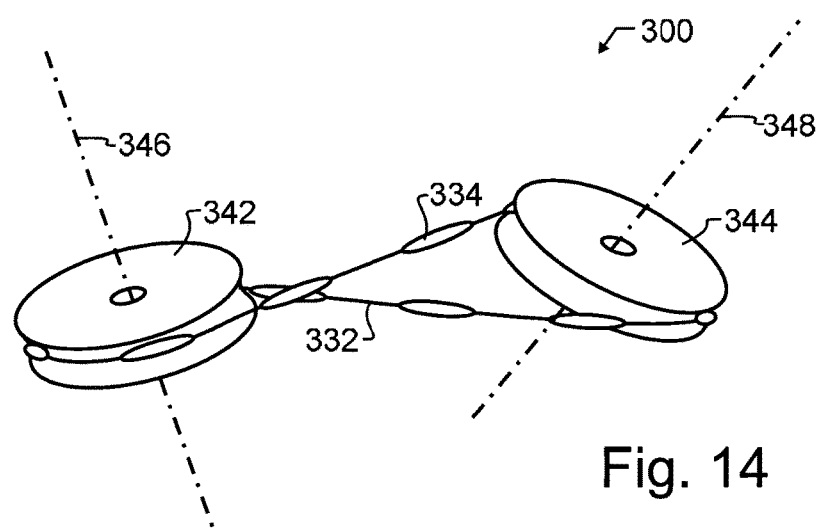
FIG. 14 illustrates a third alternative embodiment brush designed in accord with the teachings of the present invention from a simplified projected view.

FIG. 14 illustrates a third alternative embodiment brush 300 designed in accord with the teachings of the present invention. Similar to brush 200 of FIGS. 12 and 13, brush 300 incorporates offset axis pulleys. However, pulleys 342, 344 have no features permitting access to brush segments 332, 334, meaning brush 300 is only active in the region of bristle belt 332 between pulleys.

Figure 15:
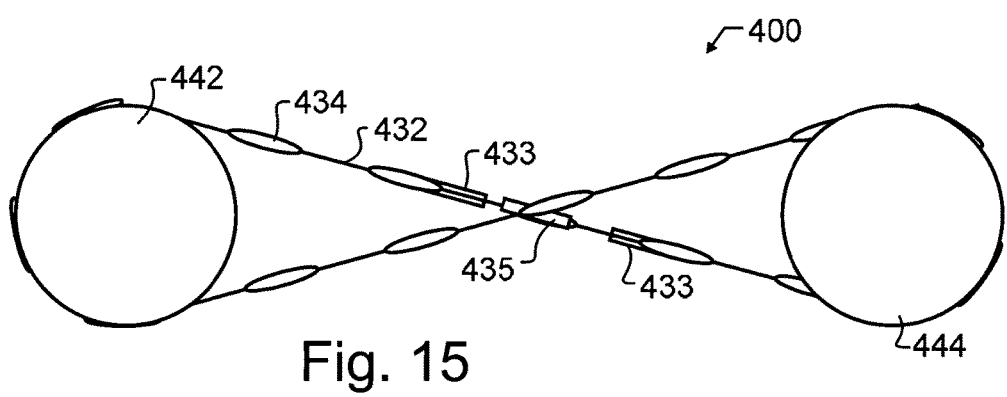
FIGS. 15 and 16 illustrates a fourth alternative embodiment brush designed in accord with the teachings of the present invention from a simplified top plan view and a simplified side elevational view.
Figure 16:
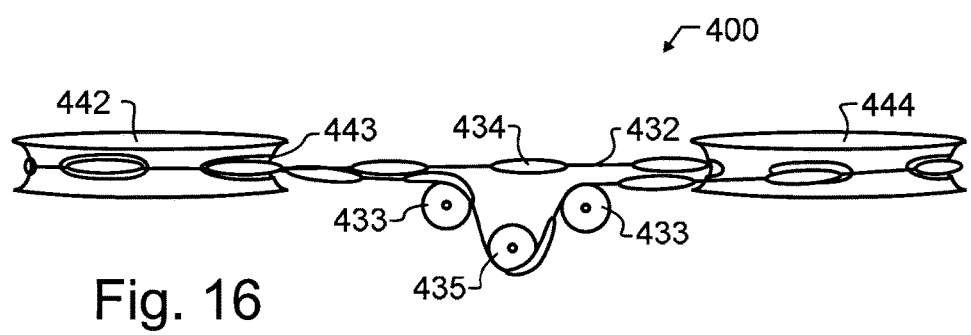

FIGS. 15 and 16 illustrates a fourth alternative embodiment brush 400 designed in accord with the teachings of the present invention. In this embodiment, brush 400 includes pulleys 442, 444 having indentations 443 to assist in positive engagement with brush segments 434, thereby increasing the drive torque before belt slippage. In addition rollers 433 and 435 are provided to guide belt 432 down in one direction adjacent to what would otherwise be the vertex, to avoid interference at the vertex.

As may be apparent then, there are a wide range of brush bristles, bristle belts, pulleys, and geometries that have been illustrated herein. While these have been illustrated in particular combinations, it should also be apparent that these components are generally adapted to be used alternatively among the various designs. So for exemplary purposes only, a number of different bristle belts have been illustrated, and could be used interchangeably across most of the brushes. Nevertheless, the bristles 64, 84, 284 are not universal, and so can only be used on some of the illustrated brushes. Such opportunities for substitution, and limitations preventing universal substitution, will be apparent to one reasonably skilled in the art upon review of the present disclosure.

Consequently, while the foregoing details what is felt to be the preferred embodiment of the invention, no material limitations to the scope of the claimed invention are intended. Further, features and design alternatives that would be obvious to one of ordinary skill in the art are considered to be incorporated herein. The scope of the invention is set forth and particularly described in the claims herein below.

I claim:

1. A brush, comprising:
    a first drive pulley having a primary loop engaging perimeter of a first diameter and defining a first axis of rotation;
    a first idler roller having a loop engaging perimeter of a second diameter smaller than said first diameter and defining a second axis of rotation, said first and second axes of rotation together defining a plane;
    a second idler roller having a loop engaging perimeter of said second diameter and defining a third axis of rotation lying within said plane;
    a second drive pulley having a primary loop engaging perimeter of said first diameter and defining a fourth axis of rotation lying within said plane, said second and third axes most adjacent in said plane and said first and fourth axes separated from each other by said second and third axes;
    a first flaccid endless loop circumscribing and engaging said first drive pulley primary loop engaging perimeter and circumscribing and engaging said first idler roller loop engaging perimeter;
    a second flaccid endless loop circumscribing and engaging said second drive pulley primary loop engaging perimeter and circumscribing and engaging said second idler roller loop engaging perimeter;
    said first and second flaccid endless loops together generally defining a lemniscate;
    a plurality of work-contacting segments protruding from and carried by said first and second flaccid loops; and
    a mechanical drive counter-rotating said first and second drive pulleys and thereby counter-rotating said first and second flaccid endless loops.

2. The brush of claim 1, wherein said plurality of work-contacting segments are comprised by bristles.

3. The brush of claim 2, wherein said bristles extend longitudinally parallel to said first axis.

4. The brush of claim 1, wherein said mechanical drive is reversible.

5. The brush of claim 1, wherein said mechanical drive is spring tensioned to tension each of said flaccid loops.

6. The brush of claim 1, wherein each of said first and second flaccid endless loops further comprises an endless belt.

7. The brush of claim 1, further comprising:
    a first drive pulley secondary loop engaging perimeter of a third diameter less than said first diameter and rotating about said first axis of rotation;
    a third idler roller having a loop engaging perimeter of a fourth diameter less than said third diameter and defining a fifth axis of rotation lying within said plane between said first and second axes of rotation; and
    a third flaccid endless loop circumscribing and engaging said first drive pulley secondary loop engaging perimeter and circumscribing and engaging said third idler roller loop engaging perimeter.

8. The brush of claim 7, wherein said mechanical drive counter-rotates said first and third flaccid endless loops.

9. The brush of claim 8, further comprising:
    a second drive pulley secondary loop engaging perimeter of said third diameter less than said first diameter and rotating about said fourth axis of rotation;
    a fourth idler roller having a loop engaging perimeter of said fourth diameter and defining a sixth axis of rotation lying within said plane between said third and fourth axes of rotation; and
    a fourth flaccid endless loop circumscribing and engaging said second drive pulley secondary loop engaging perimeter and circumscribing and engaging said fourth idler roller loop engaging perimeter.

10. The brush of claim 9, wherein said mechanical drive counter-rotates said second and fourth flaccid endless loops.

11. A brush, comprising:
    a first drive pulley having a primary loop engaging perimeter of a first diameter and defining a first axis of rotation;
    a first idler roller having a loop engaging perimeter of a second diameter smaller than said first diameter and defining a second axis of rotation, said first and second axes of rotation together defining a plane;
    a second idler roller having a loop engaging perimeter of said second diameter and defining a third axis of rotation lying within said plane;
    a second drive pulley having a primary loop engaging perimeter of said first diameter and defining a fourth axis of rotation lying within said plane, said second and third axes most adjacent in said plane and said first and fourth axes separated from each other by said second and third axes;
    a first flaccid endless loop circumscribing and engaging said first drive pulley primary loop engaging perimeter and circumscribing and engaging said first idler roller loop engaging perimeter;
    a second flaccid endless loop circumscribing and engaging said second drive pulley primary loop engaging perimeter and circumscribing and engaging said second idler roller loop engaging perimeter;
    said first and second flaccid endless loops together generally defining a lemniscate;
    a plurality of bristles protruding from and carried by said first and second flaccid loops;
    a first drive pulley secondary loop engaging perimeter of a third diameter less than said first diameter and rotating about said first axis of rotation;
    a third idler roller having a loop engaging perimeter of a fourth diameter less than said third diameter and defining a fifth axis of rotation lying within said plane between said first and second axes of rotation;
    a third flaccid endless loop circumscribing and engaging said first drive pulley secondary loop engaging perimeter and circumscribing and engaging said third idler roller loop engaging perimeter;
    a second drive pulley secondary loop engaging perimeter of said third diameter less than said first diameter and rotating about said fourth axis of rotation;
    a fourth idler roller having a loop engaging perimeter of said fourth diameter and defining a sixth axis of rotation lying within said plane between said third and fourth axes of rotation;

a fourth flaccid endless loop circumscribing and engaging said second drive pulley secondary loop engaging perimeter and circumscribing and engaging said fourth idler roller loop engaging perimeter; and a mechanical drive counter-rotating said first and second drive pulley primary loop engaging perimeters and thereby counter-rotating said first and second flaccid endless loops, counter-rotating said first drive pulley primary loop engaging perimeter and said first drive pulley secondary loop engaging perimeter and thereby counter-rotating said first and third flaccid endless loops, and counter-rotating said second drive pulley primary loop engaging perimeter and said second drive pulley secondary loop engaging perimeter and thereby counter-rotating said second and fourth flaccid endless loops.

12. The brush of claim 11, wherein said bristles extend longitudinally parallel to said first axis.

\* \* \* \* \*